(12) United States Patent
Longton et al.

(10) Patent No.: US 6,907,629 B2
(45) Date of Patent: Jun. 21, 2005

(54) DIAGNOSTIC IMAGING TABLETOP

(75) Inventors: Wallace A. Longton, Carlisle, PA (US); Curtis Miyamoto, Morristown, PA (US)

(73) Assignee: Diacor, Inc., Salt Lake City, UT (US)

( * ) Notice: Subject to any disclaimer, the term of this patent is extended or adjusted under 35 U.S.C. 154(b) by 225 days.

(21) Appl. No.: 10/191,185

(22) Filed: Jul. 8, 2002

(65) Prior Publication Data

US 2003/0031301 A1 Feb. 13, 2003

Related U.S. Application Data

(60) Provisional application No. 60/305,591, filed on Jul. 13, 2001, and provisional application No. 60/325,323, filed on Sep. 27, 2001.

(51) Int. Cl.[7] .................................................. A61N 5/00
(52) U.S. Cl. ..................... 5/601; 5/187; 5/724; 378/209
(58) Field of Search ................................. 378/177, 209; 5/187, 724, 601

(56) References Cited

U.S. PATENT DOCUMENTS

| | | | | |
|---|---|---|---|---|
| 3,466,439 A | * | 9/1969 | Setala | 378/65 |
| 3,751,028 A | * | 8/1973 | Scheininger et al. | 5/601 |
| 4,991,243 A | * | 2/1991 | Rottermann | 5/600 |
| 5,207,688 A | | 5/1993 | Carol | |
| 5,226,070 A | | 7/1993 | Ariba et al. | |
| 5,537,452 A | | 7/1996 | Shepherd et al. | |
| 5,537,454 A | * | 7/1996 | Korver, II | 378/65 |
| 5,622,187 A | | 4/1997 | Carol | |
| 5,632,275 A | | 5/1997 | Browne et al. | |
| 5,754,997 A | | 5/1998 | Lussi et al. | |
| 5,778,047 A | * | 7/1998 | Mansfield et al. | 378/209 |
| 6,143,003 A | | 11/2000 | Cosman | |
| 6,161,237 A | | 12/2000 | Tang et al. | |
| 6,493,417 B1 | * | 12/2002 | Baer et al. | 378/20 |

OTHER PUBLICATIONS

International Search Report.

* cited by examiner

*Primary Examiner*—Michael F. Trettel
(74) *Attorney, Agent, or Firm*—TraskBritt

(57) ABSTRACT

A tabletop useful for accurate positioning of a patient for imaging and diagnosis, so that patient positioning in subsequent medical treatments, such as radiation therapy, accurately and precisely correlates with the imaging data. The tabletop of the present invention is a solid flat tabletop adapted to fit over or as an insert in a conventional CT imaging or scan table and provides a flexible support section in which the flexible support material is tensioned to provide a vertical deflection corresponding to the vertical deflection of a flexible patient support of a treatment simulator or linear accelerator. In a preferred embodiment, the flexible support section may be removed and inserted into the treatment table to provide an exact correlation in vertical deflection during treatment.

19 Claims, 4 Drawing Sheets

DIAGNOSTIC IMAGING TABLETOP

The present application claims the benefit of provisional application U.S. Ser. No. 60/305,591 filed Jul. 13, 2001 and provisional application U.S. Ser. No. 60/325,323 filed Sep. 27, 2001.

FIELD OF THE INVENTION

This invention relates to diagnostic imaging, and particularly, computed tomography (CT) scanning. In particular, the invention relates to a tabletop useful for accurate positioning of a patient for diagnostic imaging, so that patient positioning in subsequent medical treatments, such as radiation therapy, accurately and precisely correlates with the imaging data.

BACKGROUND OF THE INVENTION

Patient positioning systems are used for accurate and reproducible positioning of a patient for radiation therapy, surgery, and other medical procedures. During these procedures, it is common to immobilize a part or parts of the patient's body. Accurate positioning of the body part is also important in initial and subsequent treatments, so that the precisely the same location of the body is exposed to the radiation each time. Therefore, different types of devices have been made to immobilize body parts and to index the body to the treatment table to assure proper and repeatable alignment for radiation therapy.

As radiation therapy becomes more precise with procedures such as 3D conformal Intensity Modulated Radiation Therapy (IMRT), it is critical that all facets of treatment planning are handled with maximum accuracy. Presently, when advanced, highly technical radiation therapy is performed, an imaging scan, such as computed tomography (CT), is obtained with the patient "in treatment position." From this scan, not only are the fields and blocking designed, but the treatment plan is calculated.

The standard CT scan table has a hard, convex upper patient support surface, as generally indicated in FIG. 1 below. In practice, this table is provided with a flexible mat which conforms to the upper convex surface of the table, the primary purpose of which is to improve patient comfort during extended scanning. While this configuration contributes to patient comfort, the convex structure of the table makes it difficult to exactly index the scanning data obtained to the conditions that will subsequently be encountered during radiation treatment. CT scans have also been performed on a standard CT scan "flat tabletop insert" to enable better positioning of the patient for advanced treatments. The flat tabletop inserts raise the patient above the level of the of the sidewalls of the CT table as shown in FIG. 1C, facilitating scanning of the entire body. This table insert is flat, very hard, allows for negligible deflection (defined as the downward movement of the tabletop) under weight of the patient, and tends to flatten the body parts to be imaged. However, in subsequent radiation oncology procedures, a mesh section of the typical radiation oncology table is usually in place in the simulator/linear accelerator during treatments. When positioning a patient for treatment, a deflection of the mesh occurs under weight of the patient, which can be as much as two to three centimeters at the maximum point.

Lack of accurate position representation at the time of the CT scan will not allow advanced radiation therapy to be as accurate as possible. Higher accuracy can be obtained if the scan is performed directly in accordance with the shape and position of the patient when positioned on the linear accelerator table, especially as the accuracy in IMRT and the like equipment improves and provides greater accuracy and adjustability in treatment and treatment planning.

Current problems with accurate and precise patient positioning for radiation therapy include deflection in treatment/simulator table that is different from deflection in a table used for imaging, variations in patient location on the linear accelerator table varying from day to day, lack of alignment (leveling) of table inserts used in imaging, and the fact that many facilities have already purchased and scan using table inserts that do not possess deflection capabilities. Every CT, simulator, and linear accelerator deflection should match if the patient is to be treated accurately and reproducibly.

SUMMARY OF THE INVENTION

In accordance with the present invention, there is provided a tabletop for positioning a patient for 3-dimensional imaging of a body part comprising (a) a flat patient support having an upper patient support surface and a lower surface, a width less than the width of an aperture in an imaging device through which the tabletop must travel for imaging of body parts, and a length sufficient to support a patient thereon; and (b) a section of said support which comprises a flexible support panel for the body part to be imaged. This flexible support panel comprises a radiolucent flexible fabric or mesh material tensioned to provide a predetermined vertical deflection when a patient is positioned thereon, wherein the vertical deflection corresponds to the vertical deflection of a flexible patient support of a treatment simulator or linear accelerator. A tabletop of the present invention may also include a measuring or indexing means along the perimeter of said flexible support panel for establishing the exact positioning of a patient relative to the length of said support panel.

The tabletop of the present invention may also include means to provide for accurate leveling of the table, adaptations to mount and slide the table top over an existing imaging table, and for removal and/or replacement of the flexible section of the tabletop.

While the present invention is primarily described with reference to CT scans, it is equally applicable to other imaging technologies and methods, for example, magnetic resonance imaging (MRI), nuclear medicine (molecular imaging), positron emission tomography (PET), and ultrasound.

DETAILED DESCRIPTION OF THE INVENTION

Figure 1A:
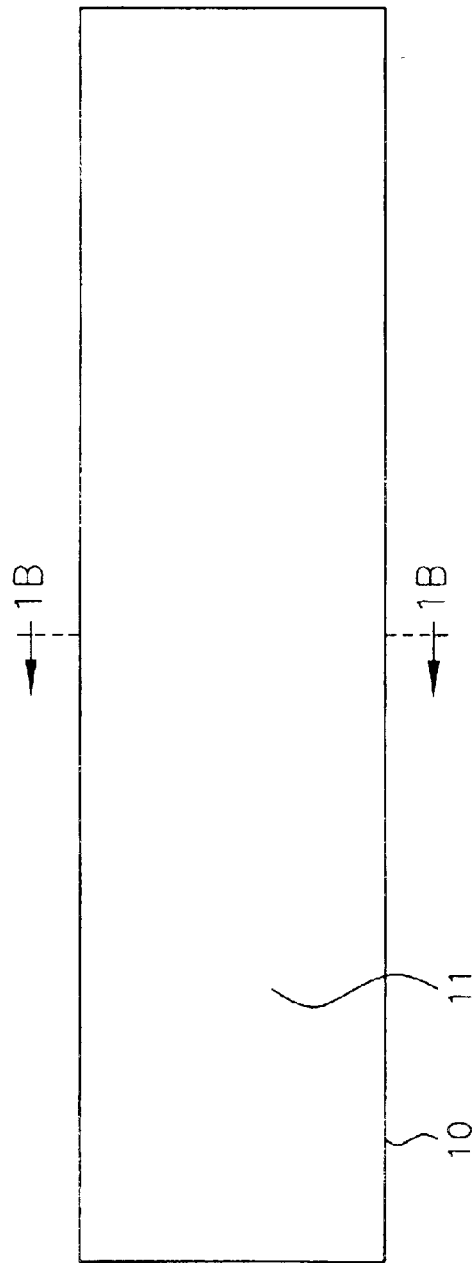
FIG. 1 is an illustration of a typical prior art CT scan table and table insert.
Figure 1C:
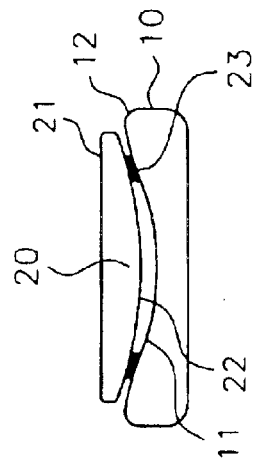
Figure 1B:

In the description which follows the present invention is described with particular reference to the typical CT scan table illustrated generally in FIGS. 1A and 1B. The table 10 has a concave top surface 11 upon which a patient rests. A soft cushion and/or a sanitary covering (not shown) can be placed on the concave top surface 11 of the table. The concavity of the upper surface 11 prevents effective imaging of body parts resting on concave surface 11 and complicates correlation of imaging data to conditions that will be subsequently encountered during radiation treatment.

FIG. 1C illustrates a typical CT scan table 10, upon which a flat-top insert 20 has been placed, for the purpose of raising the position of a patient for more accurate imaging. As shown in FIG. 1C, the tabletop insert has a hard, inflexible flat upper patient support surface 21 and a convex lower surface 22 substantially conforming to the concavity of the CT scan table 10. It is positioned on and above the concave surface on support pads 23 which are mounted on lower surface 22. As shown in the drawing, upper surface 21 is elevated above and overlaps sidewalls 12 of the CT tabletop.

Figure 2A:
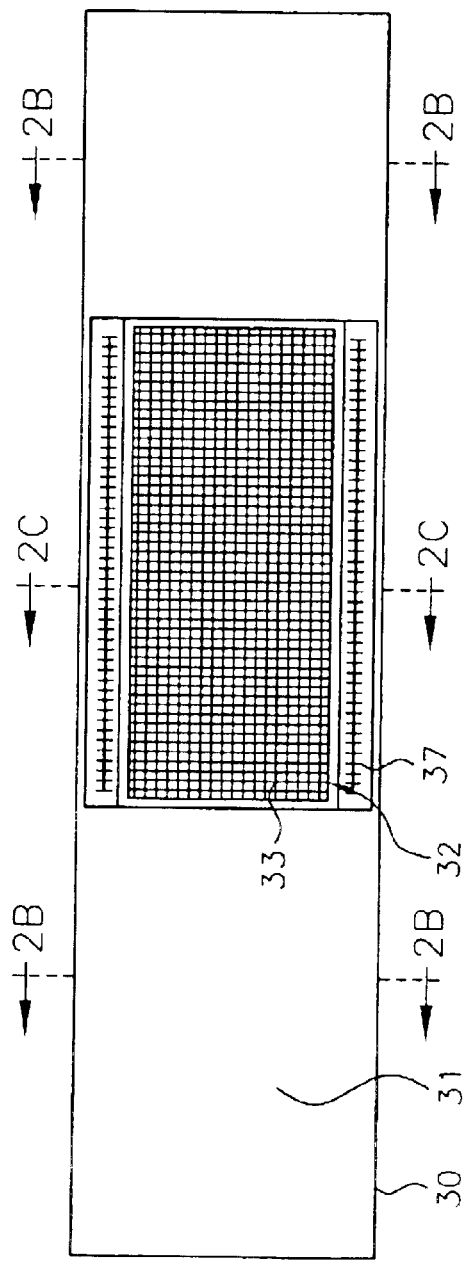
FIG. 2 is an illustration of a tabletop of the invention in which the tabletop contains a flexible, indexed support panel or section.
Figure 2C:
Figure 2B:
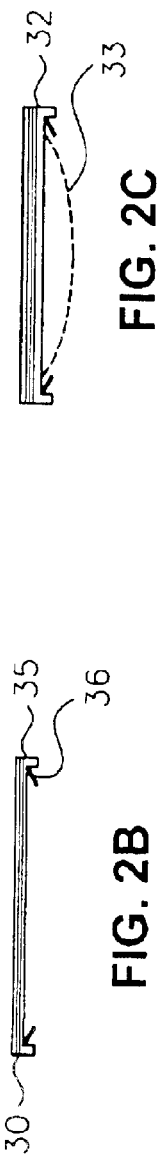
Figure 2D:
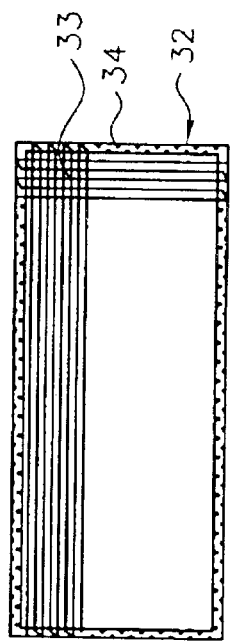
Figure 3:
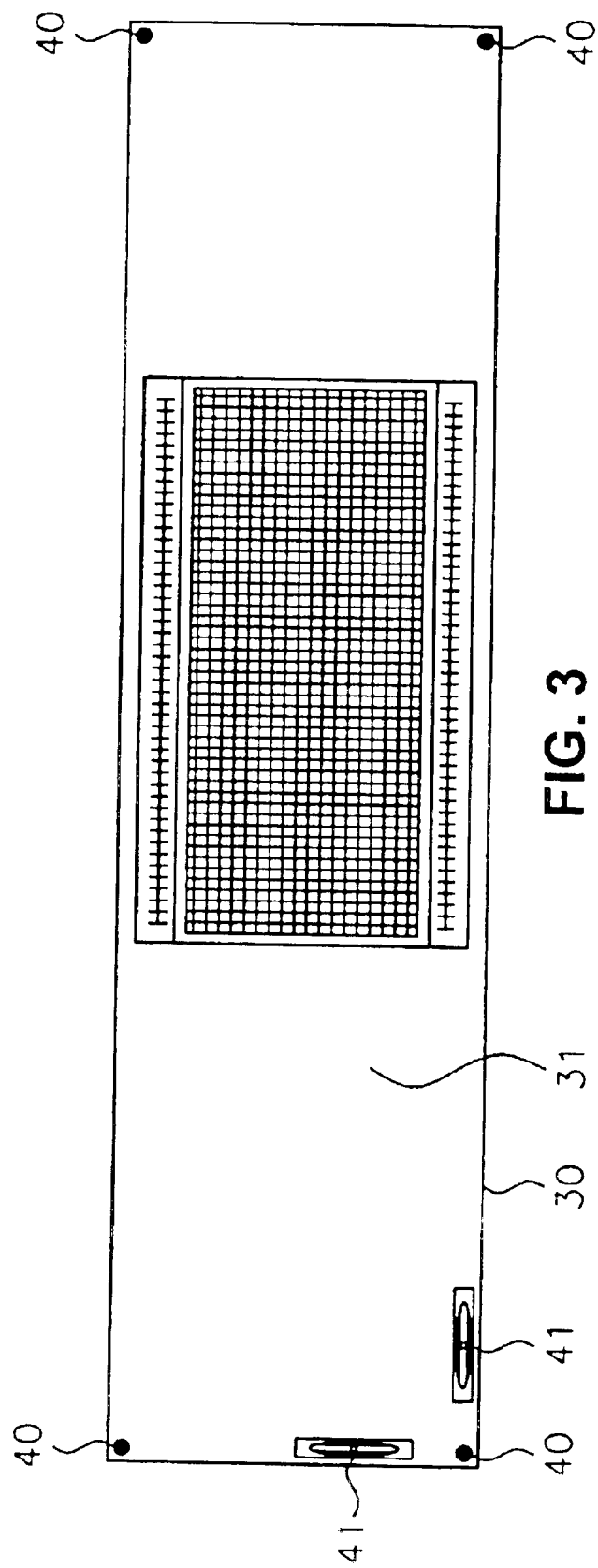
FIG. 3 is an illustration of a tabletop insert of the invention in which the tabletop contains a flexible, indexed support panel or section and means for leveling the tabletop in a horizontal position.
Figure 4:
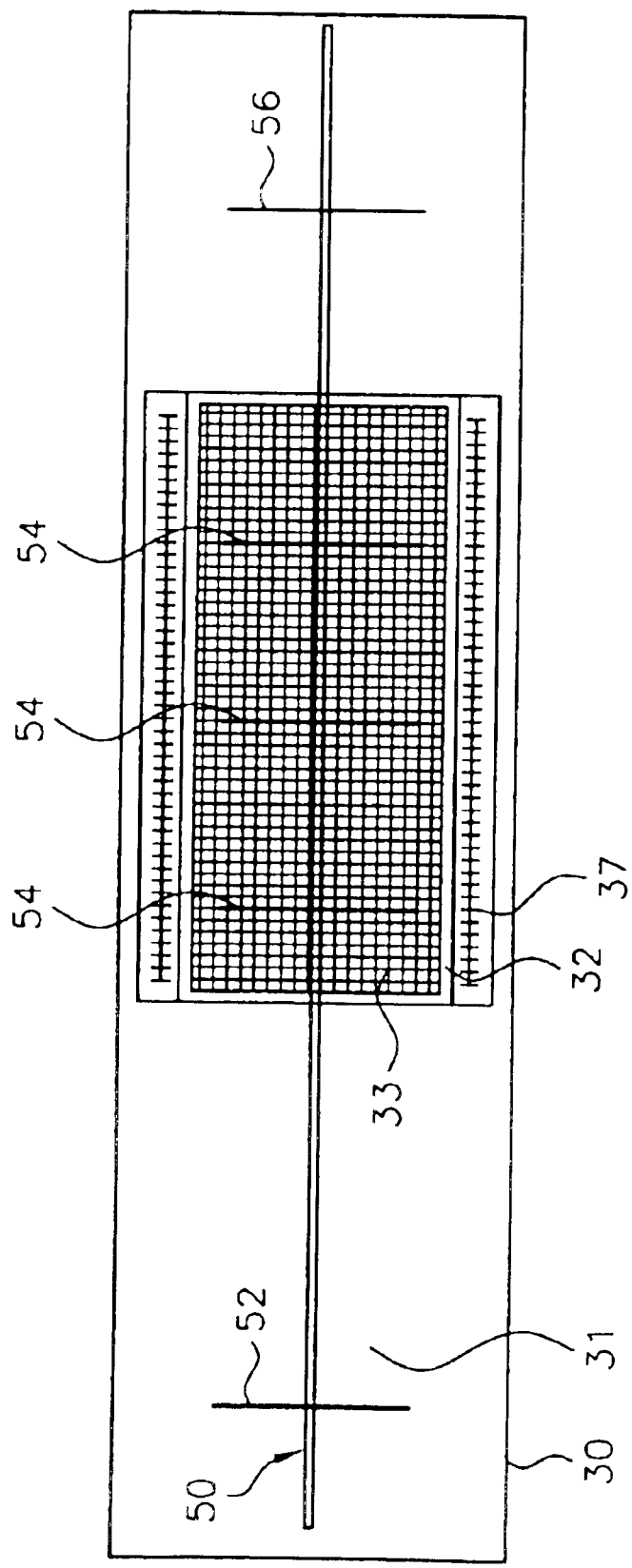
FIG. 4 is an illustration of a tabletop of the invention in which patient position markers are shown.

A tabletop of the present invention, which is particularly useful for accurate and precise repeated patient positioning for diagnostic procedures, is illustrated in FIGS. 2, 3 and 4. FIG. 2A illustrates a tabletop 30 having a flat (planar) upper patient support surface 31, a width less than the width of an aperture in an imaging device through which the tabletop must travel for imaging of body parts and a length sufficient to support a patient thereon. Tabletop 30 of the present invention also has a defined bottom surface which is suitably but not necessarily parallel to the top surface 31.

A section of tabletop 30 has a flexible support panel 32 for the body part to be imaged. The flexible support component 33 of the panel is necessarily made of a radiolucent flexible component, which can be material, fabric, or mesh. Suitable radiolucent materials include, but are not limited to carbon fiber, plastic, rubber, nylon, or other materials well-known in the art.

The flexible support component 33 is tensioned to provide a predetermined vertical deflection when a patient is positioned thereon. The vertical deflection is predetermined to match the vertical deflection of a flexible patient support portion of a treatment simulator or linear accelerator and is generally in the range of up to 0.5 to 2 cm at the maximum point of deflection when the weight of a patient is positioned thereon. To further insure accuracy in deflection of flexible support 33, a stop may be positioned below the bottom surface of the tabletop to limit deflection of flexible support 33.

The flexible support panel 32 of the invention is preferably a removable piece, which can be removed from the tabletop 30 and replaced with a solid insert, or with another flexible support panel of compatible size and shape, if so desired.

The removable flexible support panel may, for example, be sized such that it may be placed on an appropriately configured irradiation treatment table for radiation treatments. Thus, the removable support panel may be configured so that the same support, or similarly configured supports can be used for both imaging and radiation treatment procedures. The ability for interchanging the flexible support panel between the imaging and treatment tables provides additional consistency in the patient positioning for precise treatment application.

Typically, however, the flexible support panel consists of a flexible component 33, as described above and shown in FIG. 2C, connected to a frame 34, as illustrated in FIG. 2D. The flexible component 33 can be adjustably tensioned on the frame 34 to adjust the amount of deflection upon load bearing. For example, a suitable string or yarn may be strung through holes in the frame 34 of panel 32 similar to the stringing of a tennis racket, as shown in FIG. 2D. In another embodiment, a fabric used as the flexible component 32 may be held in place on the frame 34 with a groove and spline, similar to the way a screen window is fixed to a frame. Other methods for affixing the mesh to the frame will be apparent to those skilled in the art. A tabletop 30 of the invention may also be designed such that the flexible support panel 33 is an integral, non-removable part of tabletop 30. In such an embodiment, flexible support 33 is directly attached to tabletop 30. In this embodiment, flexible support 33 may be tensioned to provide a predetermined deflection and may be made of materials as described above.

Tabletop 30 of the invention may be designed to accept support panel 32, in much the same way a screen window fits into a window opening in a house. There may be an opening in tabletop 30, wherein the periphery of the opening has rabbet edges to accept a mating surface of support panel frame 34. Alternatively, the opening in the tabletop 30 may be beveled, with the wider portion of the bevel at the top surface 31, and a corresponding bevel on the outer edges of frame 34 to mate with the corresponding bevel in the tabletop. Other well known means for retaining the frame the tabletop opening will be apparent to those skilled in art. Regardless of the means used for retaining the frame in the tabletop. In a typical embodiment of the invention, the flexible support panel 32 will remain approximately flush with the plane of the top surface 31 of the tabletop. However, the flexible support panel 32 may rest lower or higher than the plane of the top surface 31 of a tabletop of the present invention.

Tabletop 30 of the present invention also has, along the perimeter of the flexible support panel 32, a means for indexing 37 the exact position of a patient relative to the length and optionally the width of the support panel. An indexing means or ruler 37 may be provided along at least one edge of support panel 32, and may extend around the perimeter of the support panel. In one embodiment, an indexing means 37 may be part of or attached to the upper surface 31 of tabletop 30. In another embodiment, indexing means 34 may be part of or attached to the frame of flexible support panel 32. In any embodiment, indexing means 34 may be either radiolucent or radiopaque.

The support panel 32 is preferably adapted to be positioned in the tabletop 30 so that the center of the support panel is in alignment with the longitudinal center of the tabletop. In another aspect of the invention, the longitudinal center of the tabletop is provided with a visible radioopaque support marking extending along the center of the tabletop and along the centerline of the support panel, as shown at 50 of FIG. 4. There may be one or more such longitudinal lines, but one of them must extend down the centerline of the table and the support panel. One or more lateral support markings extend laterally across the flexible support to perpendicularly cross and intersect the longitudinal centerline support marking 50, as shown generally at 54 of FIG. 4, one of which is positioned at the center line of longitudinal axis of the support panel. The longitudinal and lateral support marks are preferably a visible coating on the surface of the flexible support, and are radiopaque. Radiopaque markers are preferred if it is desired to relate the patient's position relative to the support in the radioimages.

Radiopaque markers would be helpful to practitioners when, for example, the patient is aligned with the visible markers 54 on the flexible support panel, and the patient alignment is recorded or noted. A patient's position may be recorded by simply applying a mark on the patient's body at the location where the patient's skin contacts the positioning markers 54 on the support panel. However, when the positioning markers are radiopaque, any adjustment in the patient's position on the tabletop may be accurately assessed relative to the location of the makers on the radioimage. In each case the peripheral markings and/or the centerline and/or lateral support markings may contain lettered or numerical designations indicating relative lateral or longitudinal position of the patient on the support panel.

A tabletop of the present invention may also have a lateral guide rail composed of a fixed portion 35 extending downward from the outside edge of the bottom of the tabletop and a stiff, yet flexible slide rail 36 extending inward from the fixed portion 35, below the bottom of the tabletop, as illustrated in FIG. 2B. Both the lateral guide rail and the slide rail may extend along the entire length of the tabletop. The fixed portions 35 of the lateral guide rail may be designed to rest over and in close proximity to the outer edge of an existing table of a diagnostic scanning instrument upon which the tabletop of this invention is to be placed. The flexible inner portions 36 of the slide rail may be designed to rest on the outer top edge of an existing table of a diagnostic scanning instrument to facilitate lengthwise movement and adjustment along the length of the table.

It will be appreciated that the embodiment of the invention illustrated in FIG. 2 may be an overlay, i.e., a table insert for an existing imaging table. Likewise it may itself be a table top which is supported by a base suitable for supporting and leveling the table top and having other suitable mechanisms appropriate for imaging procedures, including operative components which interact with the table top to transport it into and out of the imaging device.

FIG. 3 illustrates another embodiment of the present invention. In this embodiment, a tabletop 30 may have leveling means 40 and 41 for adjusting the horizontal plane of the entire tabletop. Leg-type leveling means 40 may be embedded in the corners of the tabletop and extend downward from the bottom of the tabletop. Leveling legs 40 may extend downward from the bottom, either perpendicular to the tabletop or at an angle less than 90° but greater than 0°. Leveling legs 40 should be designed to provide sufficient clearance for deflection of the flexible insert portion 33 panel 32. In addition, the leveling means also includes at least one longitudinal level indicator and one lateral level indicator positioned on or in the surface of the tabletop. This embodiment is particularly suited for use as a tabletop to overlay an existing imaging table, facilitating appropriate leveling of the patient support surface independent of the leveling of the imaging table.

What is claimed is:

1. A tabletop for 3-dimensional imaging and positional mapping of a body part to be subsequently treated by radiation therapy comprising:
   (a) a patient support having a flat upper patient support surface, a width less than the width of an aperture in an imaging device through which the tabletop must travel for imaging of a body part, and a length sufficient to support a patient thereon; and
   (b) a section of said support surface which comprises a flexible support panel for the body part to be imaged;
   (c) said flexible support panel comprising a radiolucent flexible fabric or mesh material, said material being tensioned to provide a predetermined amount of vertical deflection when a patient is positioned thereon, wherein the amount of said vertical deflection is substantially the same as the amount of vertical deflection under like conditions of a flexible patient support panel of a treatment simulator or linear accelerator table.

2. The tabletop of claim 1, wherein said flexible support panel includes indexing means comprising a ruler along the perimeter of said flexible support panel, said ruler providing a marker for establishing the exact positioning of a patient relative to the length of said support panel.

3. The tabletop of claim 1, wherein said flexible support panel is removable from said tabletop.

4. The tabletop of claim 2, wherein said flexible support panel is removable from said tabletop.

5. The tabletop of claim 3 or 4, wherein said flexible support panel may be removed and placed on an irradiation treatment table for radiation treatments.

6. The tabletop of claim 3 or 4, wherein said flexible support panel comprises a frame on which said radiolucent flexible fabric or mesh material is supported.

7. The tabletop of claim 1, further comprising lateral guide rails along the underside of the length of the tabletop.

8. The tabletop of claim 7, wherein said lateral guide rails are positioned to extend over and in close proximity to the outer lateral surface of the imaging table on which the tabletop is positioned.

9. The tabletop of claim 1, further comprising slide rails positioned on the underside of said patient support, said slide rails positioned for moveable contact with the upper surface of the imaging table on which the tabletop is placed.

10. The tabletop of claim 1, wherein the tabletop includes visible leveling means for supporting said tabletop in a horizontal position, said leveling means comprising at least one longitudinal and one lateral leveling indicator.

11. The tabletop of claim 8, wherein said leveling means comprises at least one longitudinal and one lateral leveling indicator and at least one adjustable leg extending downward from the bottom of the tabletop.

12. The tabletop of claim 2 wherein the indexing means along the perimeter of the flexible support panel extend into the interior of the flexible support panel.

13. The tabletop of claims 1 or 2 wherein the flexible support panel includes at least one visible positioning marker on the flexible fabric or mesh material, said positioning marker being a radiopaque coating on the support panel.

14. The tabletop of claim 1 or 2 wherein the tabletop further comprises at least one longitudinal patient positioning marker on the upper surface of the patient support panel, said marker comprising a radiopaque material extending alone the longitudinal centerline of the patient support panel.

15. The table top of claim 14 wherein the patient positioning marker includes a marker along a centerline of the tabletop, and at least one radiopaque marker perpendicular to the centerline of the patient support panel.

16. The tabletop of claim 1, wherein said tabletop is an insert for a conventional 3-dimensional imaging table and comprises a lower surface adapted to rest upon a conventional imaging table for 3-dimensional imaging.

17. An improved system for radiation treatment of a patent in need of such treatment, including
   (A) An imaging table for positioning a patient for 3-dimensional imaging of a body part and wherein said imaging table comprises a patient support having an upper patient support surface which is concave, a width less than the width of an aperture in an imaging device through which the said patient support must travel for imaging of a body part, and a length sufficient to support a patient thereon; and
   (B) A separate treatment table for positioning a patient for radiation or simulated radiation treatments, wherein said treatment table comprises a mesh section for support of a body part to be treated, said mesh section having a vertical deflection under the weight of a patient placed thereon for treatment; and in which the improvement comprises a tabletop for said imaging table, said tabletop comprising:

(a) a patient support having a flat upper patient support surface, a lower surface adapted to rest upon conventional imaging table (A), a width less than the width of an aperture in an imaging device through which the tabletop must travel for imaging of a body part, and a length sufficient to support a patient thereon; and (b) a section of said patient support surface which comprises a flexible support panel for the body part to be imaged, said flexible support panel comprising a radiolucent flexible fabric or mesh material, said material being tensioned to provide a predetermined amount of vertical deflection when a patient is positioned thereon, wherein the amount of said vertical deflection is substantially the same as the amount of vertical deflection under like conditions of the mesh section of the simulator or treatment table.

18. The improved system of claim 17, wherein the tabletop further comprises at least one longitudinal patient positioning ruler on the upper surface of the patient support panel, said marker comprising a radiopaque material extending along the longitudinal centerline of the patient support panel.

19. The system of claim 18, wherein the patient positioning marker includes a marker along a centerline of the tabletop, and at least one radiopaque marker perpendicular to the centerline of the patient support panel.

* * * * *